US00PP35876P2

(12) United States Plant Patent
Chen

(10) Patent No.: US PP35,876 P2
(45) Date of Patent: Jun. 18, 2024

(54) ***EPIPREMNUM* PLANT NAMED 'UF-Ea-0316'**

(50) Latin Name: *Epipremnum aureum*
Varietal Denomination: UF-Ea-0316

(71) Applicant: Florida Foundation Seed Producers, Inc., Marianna, FL (US)

(72) Inventor: Jianjun Chen, Lake Mary, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/371,616

(22) Filed: Sep. 22, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP20,930 P2 4/2010 Henny et al.
PP21,217 P2 8/2010 Henny et al.

*Primary Examiner* — Susan McCormick Ewoldt
(74) *Attorney, Agent, or Firm* — Koenig IP Works, PLLC; Katherine Koenig

(57) ABSTRACT

A new and distinct cultivar of Pothos (*Epipremnum aureum*) plant named 'UF-Ea-0316', particularly distinguished by lanceolate shaped leaves having a consistent marbled green and bright white coloration across the entire leaf surface, small size plant form, and robust and extremely compact growth habit, is disclosed.

3 Drawing Sheets

Genus and species: *Epipremnum aureum.*
Cultivar denomination: 'UF-Ea-0316'.

BACKGROUND OF THE NEW CULTIVAR

*Epipremnum* Schott, commonly known as Pothos, belongs in the family Araceae and is native to the southeast Asian and Solomon Islands in the Pacific. *Epipremnum* has about 10 species, but only *E. aureum* or *E. pinnatum* 'Aureum' (Boyce, 1998) has been widely grown as an ornamental and is among the most popular foliage plants worldwide. Pothos is an important foliage plant in the commercial trade. Based on the USDA Floriculture Crops Statistics, the wholesale value of Pothos in 2018 was $22.89 million. It ranked as the third among all cultivated foliage plant genera. With the increased popularity of "living walls" since 2010, pothos has been the highest in-demand indoor foliage plant, especially demand for cultivars with contrasting and bright foliage colors. Prior to 2009, there have been only four cultivars available in commercial trade, 'Golden Pothos' (unpatented), 'Marble Queen' (unpatented), 'Jade' (unpatented), and 'Neon' (unpatented). In 2009, two new Pothos cultivars were released namely, 'UFM10' (U.S. Plant Pat. No. 20,930, commercial name Green Genie™, owned by Florida Foundation Seed Producers, Inc.) and 'UFM12' (U.S. Plant Pat. No. 21,217, commercial name Pearls and Jade®, registered trademark of Florida Foundation Seed Producers, Inc.). These two cultivars are the result of mutation breeding through exposure to gamma ray radiation.

Pothos has bisexual flowers like its relatives of *Anthurium* and *Spathiphyllum* but rarely flowers in nature. Thus, Pothos is propagated predominantly through single or double eye stem or vine cuttings. As a result, there have been no literature reports of Pothos breeding through hybridization. Since Pothos breeding through conventional hybridization is difficult, a new method was initiated for developing new Pothos cultivars through selection of mutants from regenerated populations. Pothos was first successfully regenerated from leaf and petiole explants in 2002, and subsequently, methods for regeneration of 'Golden Pothos' through direct somatic embryogenesis was accomplished in 2005, 'Marble Queen' in 2012, and as well as other Pothos cultivars. The established regeneration systems were used for isolation of mutants.

SUMMARY OF THE INVENTION

The invention relates to a new and distinct cultivar of Pothos plant named 'UF-Ea-0316'. The new cultivar 'UF-Ea-0316' originated from a regenerated population of 'Marble Queen'. Leaf explants of 'Marble Queen' were cultured on Murashige and Skoog (MS) medium supplemented with 9 μM N-phenyl-N'-1,2,3-thiadiazol-5-ylurea (TDZ) and 1 μM α-naphthalene acetic acid (NAA). Somatic embryos directly occurred on the leaf surface and on the cut ends in 4-6 weeks. Subsequent embryo conversion resulted in plantlets four weeks later. Plantlets with short internodes were selected and transplanted into plug trays filled with a substrate in a shaded greenhouse for acclimatization. Variegated plantlets were selected and transplanted in 10 cm pots filled with a substrate in a shaded greenhouse for acclimatization. Selected plants were potted in 15-cm pots for evaluation. 'UF-Ea-0316' was selected as a single plant from said regenerated population in April 2015 in Apopka, Florida due to its unique leaf shape and leaf color patterning as well as compact growth form.

The new cultivar 'UF-Ea-0316' was first propagated asexually by vegetative stem cuttings in September 2015 in Apopka, Florida and has been found to remain true-to-type and to retain its distinctive characteristics through successive asexual propagations for seven years.

Plant Breeder's Rights for the new cultivar 'UF-Ea-0316' have not been applied for, and 'UF-Ea-0316' has not been made publicly available more than one year prior to the filing date of this application.

The new cultivar 'UF-Ea-0316' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF-Ea-0316' when grown under normal horticultural practices in Apopka, Florida: Lanceolate shaped leaves having a consistent marbled green and bright white coloration across the entire leaf surface; small size plant form; and robust and extremely compact growth habit.

When compared to the parent Pothos plant 'Marble Queen', 'UF-Ea-0316' has a smaller plant form with smaller, lanceolate shape leaves, whereas 'Marble Queen' has a larger plant form with larger, cordate shaped leaves. Additionally, 'UF-Ea-0316' has a leaf internode length that is significantly smaller than the leaf internode length of 'Marble Queen'. Further, 'UF-Ea-0316' has an extremely compact growth habit, whereas 'Marble Queen' has a more trailing growth habit and is less compact.

DESCRIPTION OF THE FIGURES

This new Pothos cultivar 'UF-Ea-0316' is illustrated by the accompanying photographs, which show the plant's form and foliage. The colors shown are as true as can be reasonably obtained by conventional photographic procedures. The photographs are of seven-month old plants grown from unrooted cuttings in November 2018 in a shaded greenhouse in Apopka, Florida.

DETAILED BOTANICAL DESCRIPTION OF THE CULTIVAR

Figure 1:
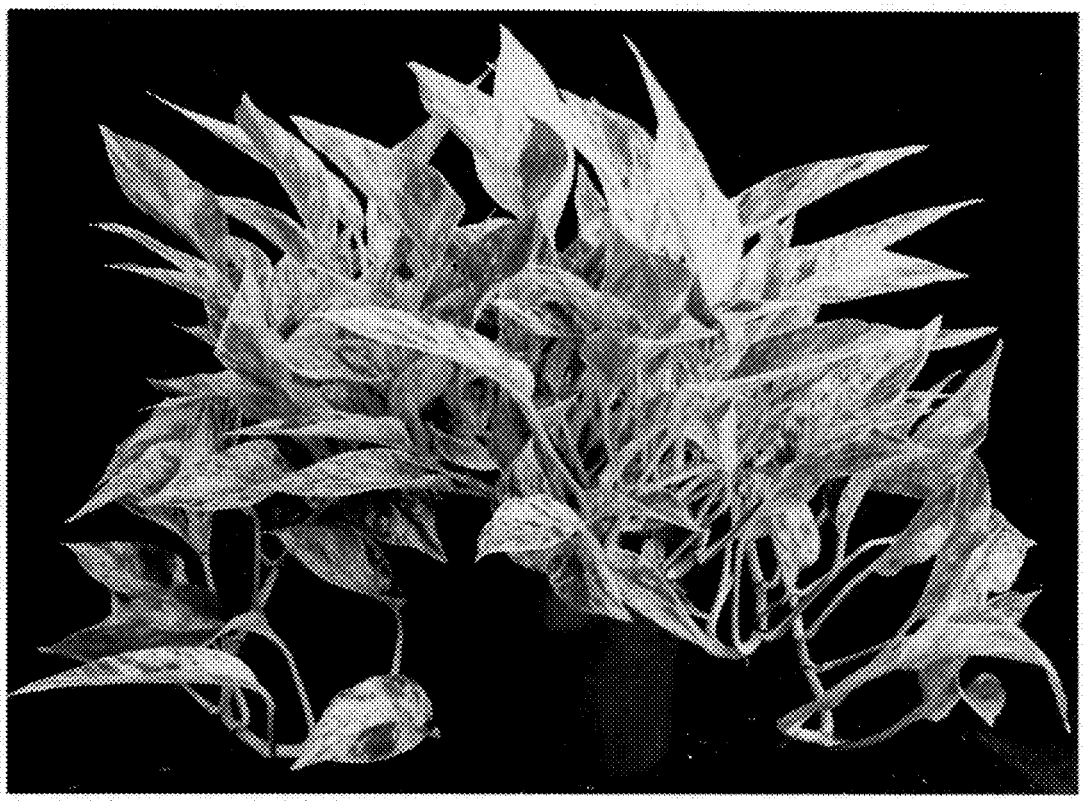
FIG. 1 shows the growth habit, form, and foliage of the new pothos cultivar 'UF-Ea-0316'.
Figure 2:
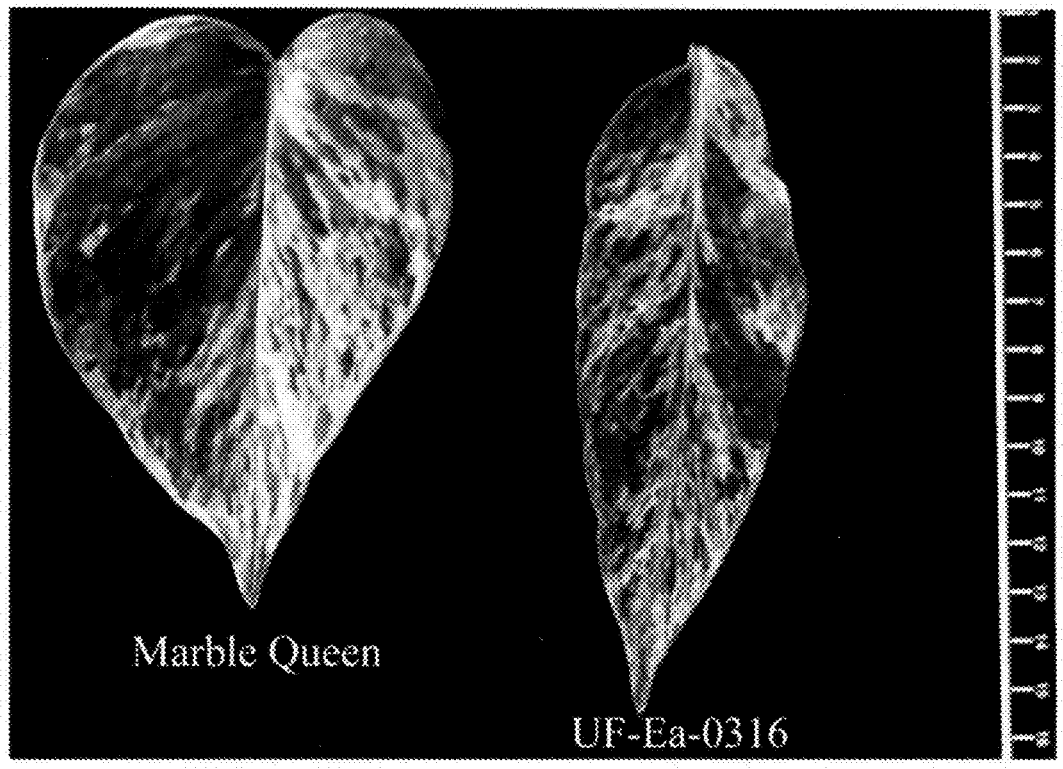
FIG. 2 shows a side-by-side comparison of the adaxial surface of a leaf of 'UF-Ea-0316' (right) and 'Marble Queen' (left)
Figure 3:
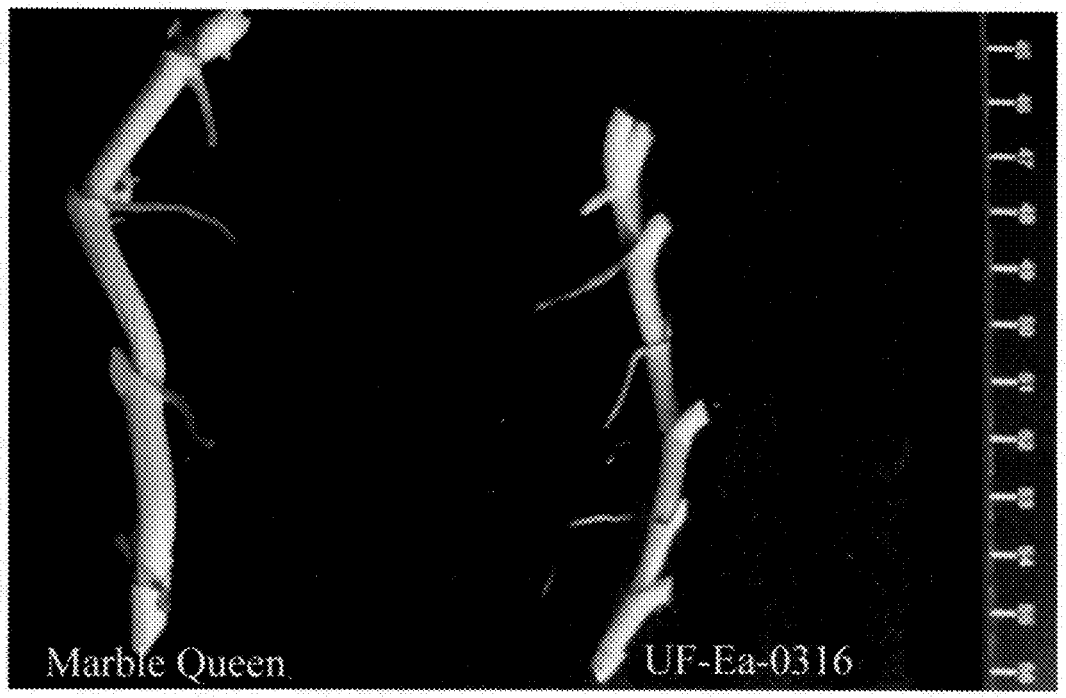
FIG. 3 shows a side-by-side comparison of a stem of 'UF-Ea-0316' (right) and 'Marble Queen' (left).

Foliage color was determined under full sun conditions in the middle of the day in a shaded greenhouse with 75% light exclusion. Color references are to the RHS Colour Chart of The Royal Horticultural Society of London (RHS), 2007 5$^{th}$ Edition. The following detailed description of 'UF-Ea-0316' was obtained using seven-month old plants grown from unrooted cuttings in November 2018 in a shaded greenhouse in Apopka, Florida. Single eye or double eye cuttings from stems were directly rooted in either 15-cm pots (10-15 cuttings per pot) or 20-cm pots (15-20 cuttings per pot) filled with commercial substrates generally comprised of 60% peat, 20% perlite, and 20% vermiculite based on volume. Cuttings rooted in 2-3 weeks in the shaded greenhouse. After rooting, plants were fertilized with a controlled-release fertilizer (15-9-12) at 5 g per 15-cm pot and 8 g per 20-cm pot and grown for an additional 25 weeks.

Botanical description:

Botanical classification:

*Family.*—Araceae.

*Botanical name.*—*Epipremnum aureum.*

*Common name.*—Pothos.

*Cultivar.*—'UF-Ea-0316'.

Plant description:

*Plant type.*—Perennial tropical vine.

*Growth habit.*—Extremely compact with vines largely twined together rather than training.

*Height from soil level to top of foliar plane.*—Approximately 20 cm.

*Growth rate.*—Slow.

*Branching characteristics.*—One main stem (vine), weak basal branching.

*Vine length.*—Approximately 15 cm on a 3-month-old plant.

*Vine diameter.*—Approximately 0.5 cm.

*Internode length.*—1.5 to 2.0 cm on a 3-month-old plant.

*Texture of vines.*—Glabrous and striated.

*Shape of vines.*—Predominantly round and slightly flattened on one side.

*Color of vines.*—Green (127C) and light green (130C) with some white (NN155D) linear striations.

*Number of leaves per vine.*—7 to 8 on a 3-month old plant.

Propagation:

*Type cuttings.*—Vegetative stem cuttings having at least 1 node.

*Time to initiate roots.*—21 days.

*Time to produce a rooted cutting.*—21 weeks after root establishment.

*Root habit.*—One aerial root oriented downwards and present at each stem node, aerial roots produce fine roots when in contact with soil.

*Root description.*—Aerial roots are about 3 cm in length and 2 mm in diameter, colored brown (165A), soil roots are about 0.5 mm in diameter and colored white (NN155D).

Foliage description:

*Arrangement.*—Alternate.

*Attachment.*—Petiolate.

*Leaf.*—Shape: Lanceolate. Length: Approximately 12 cm. Width: Approximately 4 cm. Apex shape: Narrowly acuminate. Base shape: Oblique. Texture (upper surface): Glabrous and leathery. Texture (lower surface): Glabrous and leathery. Orientation: Newly expanded leaves are held erect and upwards, mature leaves are more horizontal to slightly upwards. Margins: Entire. Color: On mature leaves, bright white (NN155D), greyed green (191A), and green (137A) in irregular blotches and strips. White patches on young and recently fully-expanded leaves often appear light-yellow (157D) in color. Young leaves have more intensive variegation than do the older leaves. The variegation is visible on both the adaxial and abaxial surfaces, but the greyed-green (191A) may not be visible on the abaxial surface of older leaves. Leaf sheen: Upper surface: Slightly shiny. Lower surface: Slightly shiny. Venation: Pattern: Eucamptodromous. Color: Upper surface white (NN155D) or green (141A). Lower surface green (141A).

*Petiole.*—Length: 7 to 10 cm. Width: Approximately 0.35 cm. Color: Whitish green (125D) with green (RHS 140A) linear striations.

Inflorescence: None observed to date.

Fruit and seed set: None observed to date.

Disease and insect resistance: None observed to date.

Cold tolerance: Tolerant down to 5° C.

Drought tolerance: Tolerant.

Comparison with known cultivars: 'Marble Queen' (unpatented) is the best commercial comparison. When compared to 'Marble Queen', the new cultivar 'UF-Ea-0316' has a smaller plant form with smaller, lanceolate shape leaves, whereas 'Marble Queen' has a larger plant form with larger, cordate shaped leaves. Additionally, 'UF-Ea-0316' has a leaf internode length that is significantly smaller than the leaf internode length of 'Marble Queen'. Further, 'UF-Ea-0316' has an extremely compact growth habit, whereas 'Marble Queen' has a more trailing growth habit and is less compact.

What is claimed is:

1. A new and distinct *Epipremnum* plant named 'UF-Ea-0316' as illustrated and described herein.

* * * * *